United States Patent [19]

Skubitz et al.

[11] Patent Number: 5,438,075

[45] Date of Patent: Aug. 1, 1995

[54] ORAL GLUTAMINE TO REDUCE STOMATITIS

[76] Inventors: Keith M. Skubitz, 2915 W. 43rd St., Minneapolis, Minn. 55410; Peter M. Anderson, 2809 Louisiana, St. Louis Park, Minn. 55426

[21] Appl. No.: 39,905

[22] Filed: Mar. 30, 1993

[51] Int. Cl.$^6$ .......................................... A61K 31/195
[52] U.S. Cl. .................................................. 514/563
[58] Field of Search ........................................ 514/563

[56] References Cited

U.S. PATENT DOCUMENTS 5,039,704  8/1991  Smith et al. ......................... 514/563

OTHER PUBLICATIONS

"A Review of the Effects of Glutamine Enriched Diets on Experimentally Induced Enterocolitis", vol. 14, No. 4, Supplement in Journal of Parenteral and Enteral Nutrition. (1990).

"Oral Glutamine Reduces Bacterial Translocation following Abdominal Radiation" by Wiley Souba et al in Journal of Surgical Research 48, 1–5 (1990).

"Effect of a Glutamine Supplemented Enteral Diet on Methotrexate-Induced Enterocolitis" by Andrew D. Fox in Journal of Parenteral and Enteral Nutrition, 12(4):325–331 (1988).

"Dietary Manipulation of Methotrexate-Induced Enterocolitis" by Jin Shou et al in Journal of Parenteral and Enteral Nutrition vol. 15, No. 3, p. 307, (1991).

"Does Glutamine Contribute to Immunosuppression after major burns" by Mark Parry-Billings et al in The Lancet, vol. 336:523–525 (1990).

"Glutamine Nutrition and Requirements" by Robert J. Smith et al in Journal of Parenteral and Enteral Nutrition vol. 14, No. 4 Supplement, Jul./Aug. 1990.

"New Fuels For the Gut" by Sarah T. O'Dwyer in Chemical Tube Feeding, 1990.

"Clinical and Metabolic Efficacy of Glutamine Supplemented Parenteral Nutrition after Bone Marrow Transplantation" by Thomas Ziegler et al in Ann. Int. Med. 116:821–828, (1992).

"Combined Effects of Glutamine and Epidermal Growth Factor on the Rat Intestine" by Danny O. Jacobs, et al in Surgery, p. 558. vol. 104, No. 2 (Aug., 1988).

"Total Parenteral Nutrition, Glutamine and Tumor Growth" by Josef E. Fischer in J. Parenter. Enteral. Nutr. 14:86S–89S, (1990).

Abstract: Effect of Route of Glutamine Administration GM Mortality Following Experimental Enterocolitis, by D. J. Burke, 14th Clinical Congress Abstract col. 14, No. 1, Supplement. (1990).

"Reduction of The severity of Enterocolitis by Glutamine-Supplemented Enteral Diets" by Andrew D. Fox et al, in Surgical Form, 1987, 38:43–44.

"Total Parenteral Nutrition and Bowel Rest Modify and Metabolic Response to Endotoxin in Humans" by Yuman Fong et al in Ann. Surg, Oct. 1989, vol. 210, No. 4.

"Glutamine Enhanced Enteral Diet Improves Nitrogen Balance Without Increasing Portal Ammonia", M. G. Brown, et al in Br. J. Surg. 1991, vol. 78, Nov. 1305–1306.

"Disparate Effects of 5–fluorouracil on the Ileum and Colon of Enterally Fed Rats with Protection by Dietary Glutamine" in Surgical Forum, p. 45. (1988).

"Ten Versus TPN Following Major Abdominal Trauma–Reduced Septic Morbidity" by Frederick A. Moore, in The Journal of Trauma, vol. 29, No. 7. (1989).

"Absorption and Metabolic Effects of Enterally Administered Glutamine in Humans", by Pierre Dechelotte, in American Physiological Society, 1991, p. G677.

(List continued on next page.)

Primary Examiner—Jerome D. Goldberg
Attorney, Agent, or Firm—Vidas, Arrett & Steinkraus

[57] ABSTRACT

Glutamine is administered orally at a rate of about 4.5 g/m$^2$ per day to treat oropharyngeal mucositis. This is administered to patients that experience or may develop oropharyngeal mucositis, especially those caused by chemotherapy or radiotherapy.

5 Claims, 1 Drawing Sheet

OTHER PUBLICATIONS

"Glutamine Nutrition in the Management of Radiation Enteritis" by Wiley Souba et al in Journal of Parenteral and Enteral Nutrition, vol. 14, No. 4, Supplement, p. 106S–107S (1990).

"Adjuvant parenteral nutrition in the patient with cancer", by Josef E. Fischer M.D., in Surgery 96:, vol. 96, No. 3, pp. 578–580. (1984).

"Effects of Nutrition on Tumor Growth and Tolerance to Chemotherapy" by Ezra Steiger et al in J. Surg. Res. 18:455–461, 1975.

"Parenteral Nutrition in Patients Receiving Cancer Chemotherapy" by American College of Physicians, a position paper in 1989 American College of Physicians, p. 734.

Abstract: Parenteral Nutrition Results in Bacterial Translocation from the Gut & Death Following Chemotherapy; J. C. Alverdy, M.D. et al from 14th Clinical Congress Abstract vol. 14, No. 1. Supplement (1990).

"Glutamine Utilization by the Small Intestine" by Herbert G. Windmueller; Adv. Enzymology 53:202–231, 1982.

"Parenteral Nutrition in Patients Receiving Cancer Chemotherapy" in 1989 Ann. Intern. Med., 110:734–736.

"Effects of Oral Supplementation of Glutamine On Small Intestinal Musosal Mass Following Resection" by John A. Vanderhoof et al in Journal of the American College of Nutrition. vol. 11:223–227 (1992).

Abstract: "5-Fluorouracil Toxicity on Small Intestinal Mucosa But Not White Blood Cells in Decreased by Glutamine", ST. O'Dwyer, T. Scott et al in Clinical Research, vol. 35 No. 3, 1987.

"The Effect of Dietary Glutamine and Dietary RNA on Ileal Flora, Ileal Histology, and Bacterial Translocation in Mice" by Carol L. Wells et al in Nutrition vol. 6, No. 1, 1990.

"The Gut as a Nitrogen-Processing Organ in the Metabolic Response to Critical Illness" by Wiley W. Souba, M.D., in Nutritional Support Services, vol. 8, No. 5, pp. 15–22, May 1988.

"Intestinal fuels: Glutamine, short-chain fatty acids, and dietary fiber" by Mary Ann Evans et al in Journal of the American Dietetic Association, Oct. 1992, vol. 92, No. 10, p. 1239.

"Intestinal Consumption of Intravenously Administered Fuels" by Wiley W. Souba et al in Journal of Parenteral and Enteral Nutrition., 1985, vol. 9, No. 1.

"Glutamine Nutrition Theoretical Considerations and Therapeutic Impact" by Wiley W. Souba et al in Journal of Parenteral and Enteral Nutrition., 1990, vol. 14, No. 5, Supplement.

"Effects of Glutamine-Supplemented Diets on Immunology of the Gut" by John G. Alverdy, Journal of Parenteral and Enteral Nutrition 1990 vol. 14, No. 4 Supplement.

"Oral Glutamine Accelerates Healing of the Small Intestine and Improves Outcome After Whole Abdominal Radiation" by V. Suzanne Klimberg et al in Arch Surg, vol. 125:1040–1045 (1990).

"Glutamine-Supplemented Toal Parenteral Nutrition Improves Gut Immune Function" by David J. Burke, in Archsurg, vol. 124, Dec. 1989., p. 1396.

"Intestinal Metabolism of Glutamine and Glutamate from the Lumen As Compared to Glutamine From Blood" by Herbert G. Windmueller, In Archives of Biochemistry and Biophysics, 171, 662–672 (1975).

"Respiratory Fuels and Nitrogen Metabolism in Vivo in Small Intestine and Fed Rats" by Herbert G. Windmueller et al in Journal of Biological Chemistry, vol. 255, No. 1, Jan. 1980, pp. 107–112.

"Prophylactic Glutamine Protects the Intestinal Mucosa From Radiation Injury" by V. Suzanne Klimberg, in Cancer, July 1990, vol. 66, p. 62.

"Safety and Metabolic Effects of L-Glutamine Administration of Humans" by Thomas Ziegler et al in Journal of Parenteral and Enteral Nutrition. 14:137s–146s, 1990.

"Splanchnic Exchange of Amino Acids after Amino Acid Ingestion in Patients with Chronic Renal Insufficiency[1-4]"., by Giacomo Deferrari et al in Am. J. Clin. Nutr. 48:72–83, 1988.

ORAL GLUTAMINE TO REDUCE STOMATITIS

BACKGROUND OF THE INVENTION

1. Field of the Invention

This invention relates to methods of treating oropharyngeal mucositis and other oral and nasal mucositis by oral or nasal administration of glutamine.

2. Description of the Related Art

Mucositis is a common limiting toxicity of cancer chemotherapy. While the term mucositis refers to inflammation of a mucous membrane, this term is often used synonymously with stomatitis to refer to inflammation of the oral mucosa. The strict definitions of stomatitis (inflammation of the oral mucosa), enteritis (inflammation of the intestines), and mucositis (inflammation of mucous membranes including any region of the alimentary canal) will be used to avoid confusion.

Although often a result of the bolus administration of anti-neoplastic agents, gut toxicity may be even more common when some agents are given by continuous infusion. There has been increasing interest in the administration of cancer chemotherapy by continuous infusion, since continuous infusion chemotherapy results in exposure of the tumor to cytotoxic drugs for a more prolonged period of time than does bolus administration, and may therefore be more efficacious than bolus chemotherapy for tumors with low growth fractions. However, it is clear that continuous infusion chemotherapy may have a toxicity profile different from bolus drug administration and for some drugs may be associated with more mucositis. In particular, the continuous infusion of doxorubicin is associated with less cardiotoxicity than bolus administration, but often mucositis becomes the dose limiting toxicity. Similarly, the dose-limiting toxicity of 5-fluorouracil given by bolus administration is usually leukopenia, while gut toxicity, including stomatitis and esophagitis, can become a more important toxicity when the drug is given by continuous infusion over more prolonged periods or when combined with folinic acid (Leucovorin ®). Gastrointestinal toxicity manifested by diarrhea, felt to be due to enteritis, is the major limiting toxicity of infusional FUdR.

The mechanism of chemotherapy-induced mucositis may be multifactorial. Presumably, chemotherapy damages the rapidly dividing immature intestinal crypt cells and more superficial immature mucosal cells in the oropharynx. In addition to this direct damage, it is possible that, as the mature epithelial cells are sloughed, damaged immature cells are exposed to pancreatic and biliary secretions resulting in further intestinal damage. The gut is among the largest repositories of lymphoid tissue in the body and the gut-associated lymphoid tissue has been termed GALT (Enteral Nutr. 14: 109S–113S, 1990). The effects of chemotherapy on this lymphoid tissue may result in an additional disruption to the gut mucosal integrity, in addition to the direct effects of chemotherapy on the enterocytes. Other factors may also be involved; in normal individuals there is a constant and closely regulated flow of energy, mediated by various metabolites, among different tissues in the body (Adv. Enzymology 53:202–231, 1982). Chemotherapy may directly, or indirectly via decreasing nutrient intake, alter the production by another body compartment of a metabolite necessary for the gut, for example glutamine (see below). Such an effect can be seen during catabolic illness when the plasma glutamine concentration often falls. Although perhaps more the result, rather than the cause, of mucositis, the phenomenon of bacterial translocation across a malfunctioning gut epithelium may also play a role in the gut-related toxicity of chemotherapy and radiotherapy.

Glutamine is the most abundant amino acid in the blood and in the total body amino acid pool, and recently there has been much interest in its role in nutrition. Glutamine serves many important functions: it is a nitrogen donor for various synthetic pathways; it is a precursor for nucleic acid and nucleotide synthesis; it plays an important role in acid-base balance as a substrate for renal ammoniagenesis; and it is the major precursor of the important neurotransmitters glutamate, an excitatory amino acid, and gamma-aminobutyric acid, an inhibitory metabolite. In addition, it is an important energy source for the immune system, especially lymphocytes and macrophages.

Glutamine is a "non-essential" amino acid in that it can be synthesized by most tissues. Skeletal muscle is probably the major source of glutamine synthesis in vivo, although this has not been quantitated. However, while the metabolism of some tissues, such as skeletal muscle and brain, yield a net synthesis and export of glutamine, cells of other tissues utilize glutamine both as a nitrogen source and also as an energy source.

Glutamine appears to be the major energy source for intestinal epithelium (Adv. Enzymology 53:202–231, 1982). The small intestine utilizes large quantities of glutamine, extracting 20–30% of the circulating glutamine in the post-absorbant state. It is noteworthy that the presence of glutamine or glutamate in the gut lumen decreases the extraction of glutamine by the intestine from arterial blood, and that most dietary glutamine is metabolized by the gut directly, demonstrating that glutamine in the gut can be utilized by the intestine without first making it available to the rest of the body through the circulation. In addition to being a primary fuel for gut enterocytes, glutamine may be essential for gut epithelium. For example, parenteral glutamine supplementation of total parenteral hyperalimentation decreases the villous atrophy associated with exclusive feeding via total parenteral nutrition. In vitro studies have shown that fetal mouse intestine is unable to differentiate to its mature phenotype unless glutamine is added to the tissue culture medium.

It has been theorized that elemental diets that provide nitrogen as amino acids and carbohydrate as simple sugars, with added vitamins and minerals, might decrease the gastrointestinal toxicity of chemotherapy by providing readily absorbable nutrients to the enterocytes directly through the intestinal lumen. In addition, they might decrease biliary and pancreatic secretions which could further damage the mucosa. Despite these theoretical benefits, elemental diets increased the toxicity of animals given methotrexate or 5-FU (J. Parenter. Enteral Nutr. 12:325–331, 1988). However, supplementation of an elemental diet with glutamine may protect the gut from both radiation and some chemotherapeutic agents. Studies in rats treated with methotrexate demonstrated that glutamine supplementation of an elemental diet resulted in less weight loss, increased mucosal weight of the jejunum and colon, longer survival, less mortality, and a lower incidence of bacteremia. A similar benefit of glutamine supplementation of an elemental diet was seen in another study of rats treated with methotrexate. Klimberg, et al treated rats with elemental diets enriched in either glutamine or glycine before administering abdominal radiotherapy. Rats in the glutamine group had a more normal mucosal structure and a higher survival rate than rats in the glycine enriched group (Cancer 66:62–68, 1990). Both animal and human studies suggest that enteral nutrition results in more normal gut function than parenteral nutrition, and in the setting of major abdominal trauma, enteral nutrition appears to reduce the incidence of septic complications compared with parenteral nutrition. Animal studies suggest that enteral glutamine supplementation yields a better survival rate than parenteral supplementation, when administered after methotrexate (Burke et al, J. Parenter. Enteral Nutr. 14(1) p. 8S, 1990).

L-glutamine has been administered safely to humans both orally and intravenously. In fasting, healthy, adult males an oral dose of 0.3 g/kg resulted in a transient increase in blood glutamine, peaking at $\sim 1300 \mu M$ at $\sim 30$–45 min and returning to baseline ($\sim 680 \mu M$) by 4 hours, with no evidence of clinical toxicity or generation of measurable toxic metabolites (ammonia or glutamate) (J. Parenter. Enteral Nutr. 14:137S–146S, 1990). An oral dose of 0.1 g/kg resulted in a peak glutamine concentration of $\sim 1000 \mu M$. In another study, the ingestion over 4 minutes of a mixture of amino acids (0.8 g/kg body weight; $\sim 0.064$ g/kg of glutamine) simulating the amino acid content of an animal protein meal, resulted in a peak increase of the arterial glutamine from $\sim 524 \mu M$ to $\sim 558 \mu M$ at 45 min, returning to baseline by 1 hour (Am. J. Clin. Nutr. 48:72–83, 1988). Similarly, the addition of 0.57 g/kg/day of L-glutamine to parenteral nutrition solutions administered for 5 days to normal subjects was well tolerated (J. Parenter. Enteral Nutr. 14:137S–146S, 1990). In this study, the plasma glutamine was 40% higher ($\sim 975$ vs $\sim 700 \mu M$) in the glutamine supplemented group after 1 week of total parenteral nutrition. Such studies are relevant since, although one might tend to view glutamine as a normal component of the diet and thus likely harmless, glutamine and its two major metabolic products, ammonia and glutamate, can cross the blood brain barrier and potentially lead to altered central nervous system function.

Forty-five adults undergoing allogeneic bone marrow transplantation for hematologic malignancies were randomized in a double blind manner to parenteral nutrition with or without parenteral glutamine supplementation. Significant benefits were seen in the glutamine treatment group including better nitrogen balance, fewer episodes of clinical infections, and a shorter median hospitalization (Ann. Int. Med. 116:821–828, 1992). In this study, with a high dosage of intravenous glutamine, no difference in the severity of oral mucositis (stomatitis) was seen.

U.S. Pat. No. 5,039,704 to Wilmore et al describes the parenteral and enteral administration (defined as stomach and lower gastrointestinal tract) of glutamine to treat catabolic dysfunctions. In the catabolic dysfunctions described, glutamine is derived through the breakdown of muscle tissue. In spite of this source from muscle, intestinal mucosal cell demand exceeds supply. Wilmore et al supplies glutamine through a feeding tube into the small intestine at a rate of at least about 21 grams per day for a 70 kg patient.

The art described in this section is not intended to constitute an admission that any patent, publication or other information referred to herein is "prior art" with respect to this invention, unless specifically designated as such. In addition, this section should not be construed to mean that a search has been made or that no other pertinent information as defined in 37 C.F.R. §1.56(a) exists.

BRIEF DESCRIPTION OF DRAWING

Figure shows chemotherapy with and without glutamine.

SUMMARY OF THE INVENTION

Figure 1:
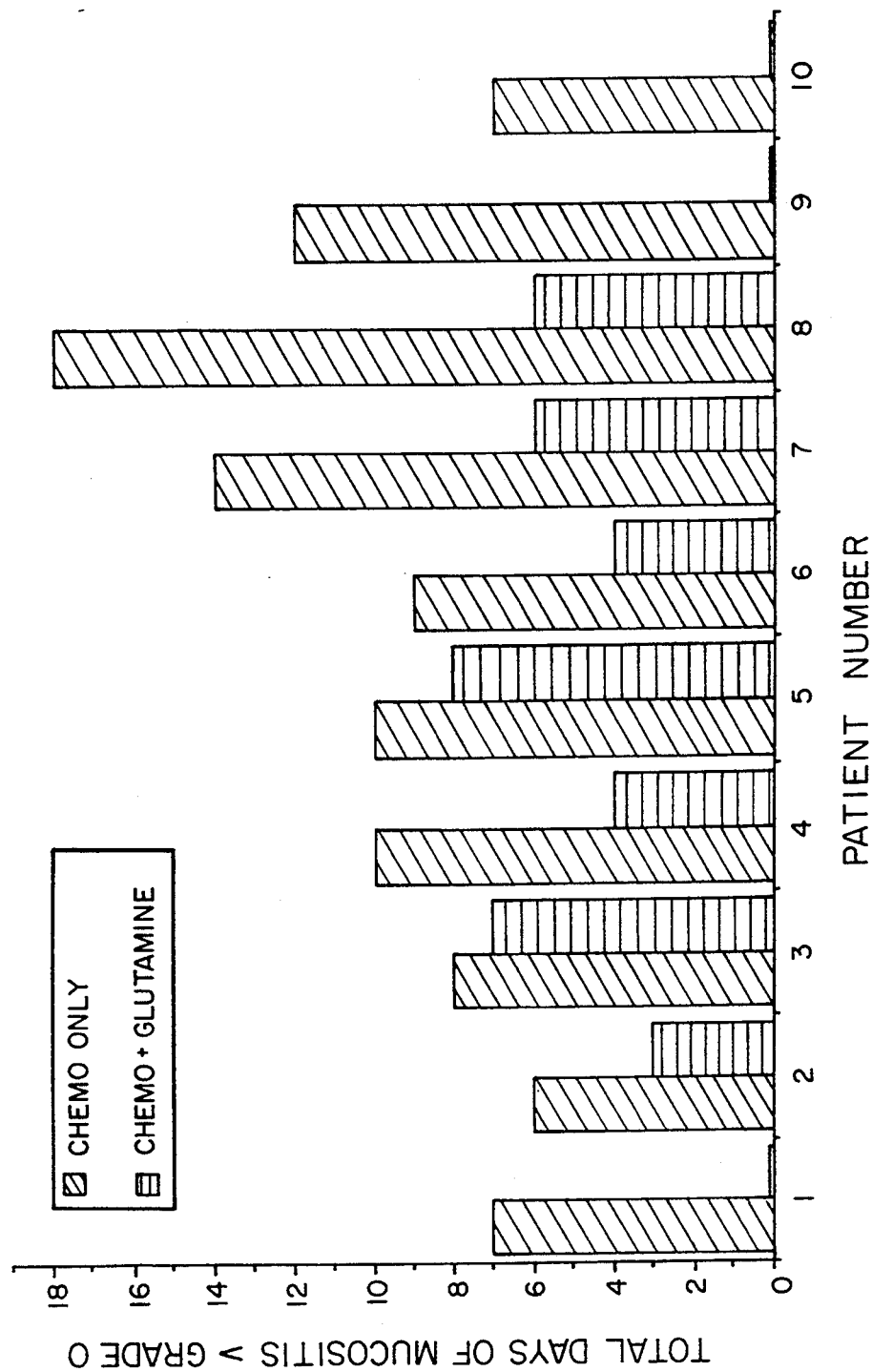

The invention provides oral and nasal administration of glutamine to patients exhibiting stomatitis or at risk of developing same. It has been found that the mucous membranes of the pharynx and mouth are protected from mucositis by oral administration of glutamine at very low dosages. Topical administration of glummine to the mouth and nasal passages should protect against mucositis in those areas.

It has been found that the damage to the oropharyngeal mucosa due to chemotherapy may be greatly decreased by taking glutamine daily at a very low dosage of between about 0.8 to 8 grams per 70 kg patient. Such doses should also work well to minimize damage due to radiotherapy. Administration of glutamine to the nasal mucosa may be accomplished by a topical spray solution, while administration to the mouth may be made via a paste, ointment, gel or gummy chew tablet or lozenge that will keep the glutamine where it is needed.

The invention provides glutamine to patients exhibiting or at risk of developing stomatitis of the oral, pharyngeal, upper esophageal, nasal and tracheal mucosa. When such patients develop stomatitis, it is often so painful that swallowing is nearly impossible. The areas to be treated by the invention may exhibit extremely painful stomatitis, which limits the ability to swallow. The glutamine is therefore supplied at a very small dosage, roughly a teaspoon in size, which may be tolerable to such patients. It is also exposed to the local mucosa directly. The glutamine is compounded with materials to be pleasant tasting in a suspension.

Since these patients are in such pain, swallowing large quantities of anything is out of the question. Enteral feeding is possible for nutrients through tubes, but causes pain and discomfort. Furthermore, tube feeding does not supply glutamine to the stomatitis-afflicted mucosa and in patients with thrombocytopenia increases the risk of nasopharyngeal, esophageal and gastric mucosal bleeding.

Since the treatment of the invention limits the severity and course of stomatitis, it increases the therapeutic index of chemotherapy and radiotherapy. Without such treatment, those regimens must be cut back in dose and often delayed since the patients cannot resume treatment until the severe pain and stomatitis resolve.

DESCRIPTION OF THE PREFERRED EMBODIMENTS

Example I

Patients experiencing mucositis of the oropharynx following a course of chemotherapy were offered the opportunity to enter this study if no other clinical parameters precluded receiving the same chemotherapy doses during the next course of treatment. Patients entering the trial received the same chemotherapy regimen as during the previous treatment, but in addition received a suspension of L-glutamine, 2 g/m$^2$ swish and swallow twice daily, from day one of chemotherapy for 28 days or for 4 days past the resolution of any post-chemotherapy mucositis. The suspension of glutamine was prepared by mixing 50 grams of L-glutamine (supplied as a crystalline powder by Ajinomoto USA, Inc., Raleigh, N.C.), with 4 parts of ORA-Sweet (Paddock Laboratories, Minneapolis, Minn.), 2 parts ORA-Plus (Paddock), and 2 parts of water to yield a suspension of 500 mg/ml L-glutamine. The final suspension contained 500 mg/ml glutamine, 30% sucrose, 2.5% glycerin, 2.8% sorbitol, 0.04% citric acid, 0.36% NaPO4, 0.16% cellulose and carboxymethylcellulose, 0.04% carrageenan, and 0.04% xanthum gum. Other carriers, flavor enhancers, gums, and suspending agents known in the art may be employed. The suspension was stored in a refrigerator during use for a maximum of 1 month.

Five parameters were documented at the end of each course of chemotherapy: 1) total number of days of mucositis, 2) severity of mucositis (numbers of days at each grade), 3) whether the use of glutamine allowed the administration of a dose of chemotherapy that would otherwise not have been tolerable without glutamine, 4) the patient's subjective impression as to whether the mucositis was less severe with glutamine supplememation, and 5) the nadir neutrophil coum. The severity of mucositis was graded as: 0, no mucositis; 1, painful mucositis not necessitating a change in oral intake; 2A, painful mucositis restricting intake to soft foods; 2B, painful mucositis restricting oral intake to liquids; and 3, mucositis preventing oral intake (CALGB criteria). Maximum grade of mucositis and total number of days of mucositis were compared by the paired t-test. All patients gave written informed consent, and the trial was approved by the Institutional Review Board of the University of Minnesota.

RESULTS

Ten adults, 5 men and 5 women, were entered in the study. All but two were treated with a 9-day continuous infusion of doxorubicin, DTIC, and cyclophosphamide with a wearable pump in the ambulatory setting as previously described; 7 of these had a soft tissue sarcoma and one a mesothelioma. One patient with AIDS and Kaposi's sarcoma was treated with doxorubicin by constant iv infusion over 5 days with bolus DTIC and vincristine. One patient with breast cancer was treated with doxorubicin, cyclophosphamide, and 5-FU, iv bolus.

TABLE 1

Effect of Oral Glutamine on Chemotherapy Induced Oral Mucositis

| Patient | Maximum Grade of Mucositis | |
|---|---|---|
| | chemotherapy only | chemotherapy + glutamine |
| 1 | 2B | 0 |
| 2 | 2A | 1 |
| 3 | 1 | 1 |
| 4 | 2A | 1 |
| 5 | 2B | 1 |
| 6 | 2B | 1 |
| 7 | 1 | 1 |
| 8 | 2A | 1 |
| 9 | 1 | 0 |
| 10 | 2B | 0 |

The severity of mucositis was graded as:
0 = no mucositis
1 = painful mucositis not necessitating a change in oral intake
2A = painful mucositis restricting intake to soft foods
2B = painful mucositis restricting oral intake to liquids
3 = mucositis preventing oral intake.

The maximum grade of mucositis decreased in 8/10 patients with glutamine supplementation (median score 2 vs 1, p=0.001) and remained the same (grade 1) in 2/10 patients (Table 1). Similarly, the total number of days of mucositis significantly decreased in 9/10 patients with glutamine supplementation (FIG. 1). Nine of the 10 patients felt that the mucositis was less severe with the addition of glutamine (Table 2). The addition of glutamine allowed the use of chemotherapy doses that would otherwise have had to be reduced due to mucositis in 8/10 patients. No change in the nadir neutrophil count was noted with the addition of glutamine.

TABLE 2

Effect of Oral Glutamine on Chemotherapy Induced Oral Mucositis
Subjective Improvement of Mucositis*

| patient | Chemotherapy + Glutamine |
|---|---|
| 1 | Yes |
| 2 | Yes |
| 3 | No |
| 4 | Yes |
| 5 | Yes |
| 6 | Yes |
| 7 | Yes |
| 8 | Yes |
| 9 | Yes |
| 10 | Yes |

*Patient's subjective interpretation of whether oral glutamine supplementation (2 gm/m$^2$ BID) was associated with less severe chemotherapy induced mucositis compared to a previous course of identical chemotherapy given without glutamine.

These results demonstrate that simple oral supplementation with glutamine can significantly decrease the severity of chemotherapy-induced stomatitis in ambulatory patients. This beneficial effect was seen in the absence of any detectable toxicity of the glutamine. It is interesting to note that the one patient (#3) who experienced no apparent benefit from the oral glutamine had mild (grade 1) mucositis and forced herself to eat normally; perhaps the additional oral glutamine in this patient represented only a small change in the oral intake of glutamine (as well as other nutrients) from her diet.

While chemotherapy can induce mucositis throughout the gut, this study examined only oropharyngeal mucositis. Since most glutamine presented to the epithelium of the small intestine is absorbed and metabolized by the gut directly, the protection of the oropharyngeal mucosa in our study raises the possibility that the oropharyngeal mucosa may also be able to absorb glutamine directly.

As with all treatments designed to decrease the toxicity of cancer chemotherapy to the host, the possibility that such treatments might also protect the tumor or even enhance tumor growth must be considered. Since glutamine is a component of the normal diet, this should be of less concern than with synthetic chemoprotective agents.

Tumor cells, like normal cells, require a source of energy. Indeed, the phenomenon of cancer cachexia, a common manifestation of malignancy, may be a protective response of the host, mediated by tumor necrosis factor (TNF) or other factors, designed to limit the availability of energy to the tumor. The risks of increasing tumor growth with parenteral nutrition have been considered, and accelerated tumor growth in animals has been demonstrated (Surgery 96:578–580, 1984; J. Parenter. Enteral Nutr. 14:86–S–89S, 1990; J. Surg. Res.

18:455461, 1975). Some human trials have also demonstrated a shortened survival and lower response rate to chemotherapy in patients with cancer receiving parenteral nutrition (Ann. Intern. Med. 110:734–736,1989). Following Warburg's demonstration that malignant cells were characterized by a high rate of aerobic glycolysis, it was assumed that glucose was the major energy source for most tumors. However, glutamine can also be used as an energy source by tumor cells. In fact, in HeLa cells glutamine has been shown to be the major energy source. Glutamine utilization by tumor cells has also been documented in vivo; in rats, a large arterial-venous gradient of glutamine was seen across the tumor bed of a Walker carcinosarcoma.

Two considerations, however, suggest that a beneficial therapeutic ratio of glutamine might be attainable. First, beneficial effects of glutamine have been seen at doses that make small contributions to the total daily caloric intake. In our human trial of oral glutamine supplementation, the glutamine contributed only ~32 calories per day to the diet. Second, and perhaps more important, the administration of glutamine orally allows the delivery of the glutamine directly to the desired tissue where it may be utilized immediately without entering the blood, and thus may not be available to the tumor. However, the predisposition of gut epithelium to utilize glutamine as an energy source suggests that a selective benefit to the host vs tumor may not be present in some patients with primary tumors of the gastrointestinal mucosa.

The beneficial effects of glutamine were seen in this invention at doses that make small contributions to the total daily caloric intake. It is of interest to note that no amelioration of myelosuppression by glutamine was detected as determined by examination of the nadir neutrophil counts. This study utilized 2 g/m$^2$ twice daily and had unexpectedly good results. The range of glutamine per kilogram of body weight being between about 0.01 to about 0.15 grams (0.30 g/m$^2$ to 4.5 g/m$^2$) as a total daily dose.

We conclude that oral glutamine supplementation is a simple, safe, and effective way to decrease the severity of mucositis induced by chemotherapy, an important cause of morbidity in the treatment of patients with cancer.

Although glutamine supplementation of enteral diets in animals had the desired effect in several studies, one study in rats suggests that the dose of glutamine may be very important. The addition of 5% glutamine to rats on a normal diet appeared to have negative effects on intestinal adaptation following massive small bowel resection, suggesting that high concentrations of glutamine in the diet could be detrimental to healing (J. Am. Coll. Nutr. 11:223–227, 1992).

Glutamine Administration

The glutamine supplied to patients in this invention may include analogs, derivatives, substitution products, isomers, or homologues which retain the characteristics of glutamine. It may be supplied orally or topically, including as a paste, gel, foam or ointment in the mouth or in the nose or as a nasal spray using the usual additives for such modes. Administration to the oropharynx is best achieved with a pleasant tasting liquid as described which may be a creme, thick syrup or the like as in cough medicines to keep the glutamine against the mucosa where it is needed. It is preferred to administer the glutamine at least twice daily.

Since pain control is one of the principal features of this invention, the glutamine must be supplied in a low volume dose, so it may be tolerated by a patient having extreme difficulty in swallowing. Accordingly, the low dose of glutamine is supplied in a pleasant tasting carrier in a total volume of less than about 15 ml. Any of the usual additives used in cough syrups or antacids may be used to make the glutamine more palatable. Suspending agents such as cellulose, carboxymethylcellulose, glycerin and carrageenan may be used along with gums and flavorants such as sucrose, sorbitol or other sweeteners.

For control of canker sores and other problems in the mouth, the glutamine may be supplied in a soft chewy tablet or as a hard candy which may be sucked to release the glutamine where needed. For children, it may be compounded into a soft chewy tablet tasting and appearing like a gummy candy. Alternatively, it may be supplied via a paste or gel to the mouth. The carriers and flavor additives typically used in toothpastes may be utilized. It should be appreciated that the quantity of glutamine needed to treat a canker sore is quite low. Accordingly, the amount of glutamine in the gel, paste or tablet may be quite low.

The invention may be used to treat aphthous stomatitis, Behcet's syndrome and canker sores of the mouth, as well as dystrophic or inflammatory lesions of the nasopharynx, mouth and esophagus. The squamous and cuboidal cells of these areas are treated by supplying glutamine orally or via other vehicles described.

A number of chemotherapy agents including doxorubicin, etoposide, 5-fluorouracil, (+/− folinic acid), methotrexate, daunomycin, actinomycin D and high doses of cytosine arabinoside are implicated in severe stomatitis and other mucositis. With the oral mucositis referred to herein, the chemotherapy must often be reduced or delayed because the pain is so severe and/or the healing process prolonged. The methods of this invention contemplate administering glutamine orally in low, tolerable doses to such patients along with the chemotherapy and/or radiotherapy. This not only limits the possible stomatitis, but allows the use of the therapy without a reduction in dose or frequency of administration.

Obviously, a reduction in chemotherapy or radiotherapy dose or frequency of administration is very undesirable, but may be required to limit stomatitis pain. The administration of glutamine increases the therapeutic index of chemotherapy and radiotherapy by lessening the associated stomatitis. This prevents the need to decrease the treatment dose intensity.

While this invention may be embodied in many different forms, there are shown in the drawings and described in detail herein specific preferred embodiments of the invention. The present disclosure is an exemplification of the principles of the invention and is not intended to limit the invention to the particular embodiments illustrated.

This completes the description of the preferred and alternate embodiments of the invention. Those skilled in the art may recognize other equivalents to the specific embodiment described herein which equivalents are intended to be encompassed by the claims attached hereto.

What is claimed is:

1. A method for treating mucositis between and including the upper esophagus and mouth in a patient in need of and undergoing bone marrow transplantation, which comprises administering to said patient glutamine or a glutamine analog orally at a rate of about 0.30 to 4.50 g/m² per day.

2. The method of claim 1 wherein said oral administration is at the rate of 0.10 to 0.13 grams of glutamine or glutamine analogue per kilogram of body weight per day and said glutamine is compounded with pleasant tasting additives to a total dose volume of less than about 15 ml.

3. A method for treating mucositis including aphthous stomatitis, canker sores, mucositis of the mouth, nasopharynx or esophagus of a patient in need of and undergoing bone marrow transplantation comprising application of glutamine or a glutamine analogue in a therapeutically effective amount in a paste, gel, ointment, or spray to the mucosa affected.

4. The method of claim 3 wherein said glutamine or glutamine analogue is compounded with a sweetener to make the administration more palatable to the patient.

5. The method of claim 4 wherein said glutamine or glutamine analogue is supplied in a soft or hard tablet form which may be chewed or otherwise kept in the mouth over the affected area.

* * * * *